United States Patent [19]

Walser et al.

[11] Patent Number: 4,752,619

[45] Date of Patent: Jun. 21, 1988

[54] NUTRITIONAL SUPPLEMENT FOR TREATMENT OF UREMIA

[75] Inventors: Mackenzie Walser, Ruxton, Md.; Henri Bermudez, Boulonge Billancourt; Claude Bordat, Dordives, both of France

[73] Assignees: The Johns Hopkins University, Baltimore, Md.; Synthelabo, Paris, France

[21] Appl. No.: 812,164

[22] Filed: Dec. 23, 1985

[51] Int. Cl.$^4$ .................. A61K 31/195; C07C 101/00; C07C 103/00

[52] U.S. Cl. .................. 514/564; 260/501.11; 514/893

[58] Field of Search .................. 514/564, 893; 260/501.11

[56] References Cited

U.S. PATENT DOCUMENTS

| | | | |
|---|---|---|---|
| 4,228,099 | 10/1980 | Walser | 260/501.11 |
| 4,296,127 | 10/1981 | Walser | 514/564 |
| 4,320,146 | 3/1982 | Walser | 514/564 |

OTHER PUBLICATIONS

Walser et al., 24, *Kidney International*, Suppl. 16, (1983), pp. S-285-S-289.
Mitch et al., 22, *Kidney International*, (1982), pp. 48–53.
Abras et al., *Metabolism and Clinical Implications of Branched Chain Amino and Ketoacids*, (1981), pp. 593–598.
Mitch et al., 31, *Clinical Research*, (1983), p. 437.

*Primary Examiner*—Stanley J. Friedman
*Attorney, Agent, or Firm*—Panitch, Schwarze, Jacobs and Nadel

[57] ABSTRACT

Mixtures of mixed salts formed between branched-chain alpha keto-acids and basic L-amino acids are useful in the nutritional treatment of chronic renal failure (uremia). These compositions contain fewer component salts than other salt mixtures containing like proportions of basic amino acids and keto acids. The compositions can be used in conjunction with a 20–30 g/day mixed quality protein diet and a vitamin and mineral supplement.

25 Claims, No Drawings

NUTRITIONAL SUPPLEMENT FOR TREATMENT OF UREMIA

BACKGROUND OF THE INVENTION

1. Field of the Invention

This invention relates to compositions for use in the nutritional treatment of chronic renal failure (uremia). More specifically, this invention relates to mixtures of mixed salts formed between branched-chain alpha-keto acids and basic L-amino acids. The compositions can be used in conjunction with a 20–30 g/day mixed quality protein diet, and a vitamin and mineral supplement.

2. Summary of the Prior Art

Salts of basic L-amino acids, such as L-arginine and L-ornithine, and alpha-keto analogs of branched-chain essential amino acids, namely alpha-ketoisocaproate, alpha-ketoisovalerate and alpha-keto-beta-methylvalerate are disclosed in U.S. Pat. Nos. 4,228,099, 4,296,127 and 4,320,146, for use in the treatment of hepatic disorders characterized by hyperammonemia and portal systemic encephalopathy, and for treatment of renal failure.

Branched-chain keto acids, and alpha-ketoisocaproate in particular, are known to exhibit a nitrogen- or protein-sparing effect in patients with chronic renal failure. That is, branched-chain keto acids reduce urinary nitrogen loss. These keto acids have been used to improve the nitrogen balance in patients suffering from a number of different nitrogen wasting conditions.

Keto acid analogs are also known to be adequate nutritional substitutes for several of the essential amino acids. Substitution of keto analogs for essential amino acids makes possible a reduction in the nitrogen intake of uremic patients Reduction in dietary nitrogen intake may produce symptomatic benefit in patients whose blood urea nitrogen concentrations are high, simply by ameliorating the toxicity of urea itself. However, the nitrogen-sparing effect of keto analogs is clinically much more significant than the anticipated reduction in blood urea nitrogen.

Ideally, the most effective nutritional regimen for the treament of chronic renal failure in the pre-dialysis phase would be one that maintains protein nutrition as well as energy balance while minimizing the intake of those components of protein-containing foods which contribute to uremic toxicity. Protein-rich diets not only increase urea levels, but also increase accumulation of phosphates, sulfates and numerous organic acids and amines, substances that contribute to uremic toxicity. Protein restriction and concomitant phosphorus restriction appear to retard the rate of progression of chronic renal insufficiency.

A number of efforts have been made to optimize the nutritional treatment of chronic renal failure. For example, a 20 to 30 g/day protein diet supplemented with essential amino acid keto-analogs as calcium salts has been used. However, this approach suffers from the fact that the calcium salts of ketoanalogs are generally unpalatable and thus must be taken as coated granules or as tablets. Also the circulating concentrations of amino acids remain abnormal on this regimen, as they do on supplements based on essential amino acids themselves.

Recently, a new dietary regimen, in which the calcium salts of keto analogs have been replaced by mixed salts formed between branched-chain alpha-keto acids and basic L-amimo acids, has been used to treat chronic renal failure. These mixed salts have been found to be more soluble and less unpalatable than the calcium salts of the keto analogs and therefore may be taken as powder dissolved in water or fruit juice. E. Abras et al., "Mixed Salts of Basic Amino Acids with Branched-Chain Keto Acids," *Metabolism and Clinical Implications of Branched Chain Amino and Ketoacids* M. Walser and J. R. Williamson eds. Elsevier/North-Holland, New York (1981) 593; W. E. Mitch et al., "Long Term Effects of New Ketoacid - Amino Acid Supplement in Patients With Chronic Renal Failure," *Kidney Int.* 22 (1982) 48–53.

A treatment regimen incorporating one of these mixtures ("EE") has been found to yield a neutral nitrogen balance, and to raise the levels of tyrosine and threonine in plasma to normal. M. Walser et al., "Supplement Containing Amino Acids and Keto Acids," *Kidney Int.* 24 (1983) S285–S289. Data sufficient to assess the progression of renal failure for six months before and during treatment with this mixture was obtained for seven patients. The results show arrested progression, on the average, during administration of the mixture. W. E. Mitch et al., "The Effects of Protein Restriction Plus Keto Acids on Progression of Chronic Renal Failure" (Abst.) *Clin. Res.* 31 (1983) 437.

However, further improvement in "EE" mixture is desirable. The "EE" mixed salt supplement is prepared by mixing ten different constituents. The large number of constituents increases the difficulty of preparation of the supplement as well as the associated costs. In addition, since the shelf life of the mixture is limited by the storage stability of the least stable of the individual constituents of the mixture, mixtures with large numbers of constituents tend to have a shorter shelf life than those with a relatively small number of constituents. Thus, it is desirable to obtain a supplement having fewer constituents and which shows the same effectiveness in arresting the progression of chronic renal failure as dietary supplement "EE."

Summary of the Invention

Improved dietary supplements, which contain fewer constituents than dietary supplement "EE", but which provide the same amounts of basic amino acids and alpha-keto analogs of branched-chain essential amino acids as dietary supplement "EE", have now been discovered. These compositions, which are useful for the nutritional treatment of chronic renal failure, comprise mixtures of salts of a basic L-amino acid and a branched-chain alpha-keto acid, these mixtures being selected from (1) a mixture of L-ornithine alpha-keto-beta-methylvalerate, L-ornithine alpha-ketoisovalerate, L-lysine alphaketoisocaproate, L-lysine alpha-keto-isovalerate, and L-histidine alpha-ketoisocaproate;

(2) a mixture of L-ornithine alpha-keto-beta-methylvalerate, L-ornithine alpha-ketoisocaproate, L-lysine alpha-ketoisocaproate, L-lysine alpha-ketoisovalerate, and L-histidine alpha-ketoisocaproate;

(3) a mixture of L-ornithine alpha-keto-beta-methylvalerate, L-ornithine alpha-ketoisocaproate, L-lysine alpha-keto-beta-methylvalerate, L-lysine alpha-ketoisovalerate and L-histidine alpha-ketoisocaproate;

(4) a mixture of L-ornithine alpha-keto-beta-methylvalerate, L-ornithine alpha-ketoisovalerate, L-lysine alpha-keto-beta-methylvalerate, L-lysine alpha-ketoisocaproate, and L-histidine alpha-ketoisocaproate;

(5) a mixture of L-ornithine alpha-ketoisocaproate, L-ornithine alpha-ketoisovalerate, L-lysine alpha-keto-beta-methylvalerate, L-lysine alpha-ketoisocaproate, and L-histidine alpha-ketoisocaproate; and (6) a mixture of L-ornithine alpha-ketoisocaproate, L-ornithine alpha-ketoisovalerate, L-lysine alpha-keto-beta-methylvalerate, L-lysine alpha-ketoisovalerate, and L-histidine alpha-ketoisocaproate.

In addition to these mixtures of mixed salts, the dietary supplements based on the mixed salts preferably contain L-tyrosine, L-threonine, and calcium D,L-alpha-hydroxy-gammamethylthiobutyrate. These dietary supplements are preferably administered in conjunction with relatively low protein (20 to 30 grams per day) diets additionally supplemented with B vitamins, ascorbic acid, and calcium, such as calcium carbonate or another calcium salt.

DETAILED DESCRIPTION OF PREFERRED EMBODIMENTS

Three basic L-amino acids namely, L-ornithine, L-lysine, and L-histidine and three branched-chain alpha-keto acid analogs of essential amino acids, namely alpha-ketoisocaproate, alpha-ketoisovalerate and alpha-keto-beta-methylvalerate, are used in preparing the mixed salt constituents of dietary supplement "EE". Nine different mixed salts may be prepared by combination of each of these basic amino acids with each of these branched-chain keto acids. Dietary supplement "EE" is prepared from seven such mixed salts. However, any dietary supplement which provides each of these basic amino acids and each of these branched-chain keto acids to the body may be prepared by using as few as five such mixed salts. Fewer than five may be required, depending upon the quantities of each of the six amino acid constituents desired.

In the case of supplement "EE," assuming that the daily dosage of L-histidine is provided by four millimoles of L-histidine alpha-ketoisocaproate, the other constituents must provide the following daily dosages: L-ornithine, 21 millimoles; L-lysine, 21 millimoles; alpha-keto-beta-methylvalerate, 14 millimoles; alpha-ketoisovalerate, 14 millimoles; and alpha-ketoisocaproate, 14 millimoles.

There are six mixed salt mixtures which yield the same dosages of basic amino acids and keto acids as does the "EE" dietary supplement and which are consistent with the choice of L-histidine alpha-ketoisocaproate as a fifth constituent. Each of the six possible mixtures of five mixed salt components omits a pair of mixed salts. The six possible mixtures may be designated as follows:

TABLE I

| Designation | Compounds Omitted |
|---|---|
| A | L—ornithine alpha-keto-beta-methylvalerate |
|   | L—lysine alpha-ketoisovalerate |
| B | L—ornithine alpha-ketoisovalerate |
|   | L—lysine alpha-keto-beta-methylvalerate |
| C | L—ornithine alpha-ketoisocaproate |
|   | L—lysine alpha-keto-beta-methylvalerate |
| D | L—ornithine alpha-ketoisocaproate |
|   | L—lysine alpha-ketoisovalerate |
| E | L—ornithine alpha-keto-beta-methylvalerate |
|   | L—lysine alpha-ketoisocaproate |
| F | L—ornithine alpha-ketoisovalerate |
|   | L—lysine alpha-ketoisocaproate |

The branched-chain essential amino acids include valine, leucine and isoleucine and their corresponding alpha-keto analogs are alpha-ketoisovaleric acid, alpha-ketoisocaproic acid, and alpha-keto-beta-methylvaleric acid. These branched-chain keto acids are commercially available as calcium and sodium salts. Methods of making keto acids are well known in the art. The free acids may be prepared from the salts by addition of excess hydrochloric acid and subsequent extraction with ether and evaporation as disclosed, for example, in U.S. Pat. No. 4,228,099.

Ornithine, lysine and histidine salts of branched-chain keto acids are prepared by combining equimolar portions of the amino acids (as free bases) with the keto acids, and precipitating the salts with ethanol. The preparation of salts of basic amino acids and alpha-keto analogs is disclosed in U.S. Pat. Nos. 4,228,099 (Column 3, line 59—Column 5, line 2) and 4,296,127 (Column 5, line 49—Column 6, line 64).

The basic L-amino acid salts of alpha-keto acid analogs of the branched-chain essential amino acids apparently do not exist to an appreciable degree in dilute solution because they dissociate into amino acid cations and keto acid anions. As disclosed in U.S. Pat. No. 4,296,127, the solubility in water of many of the basic L-amino acid salts of alpha-keto analogs is greater than that of the least soluble of the amino acid and the keto analog used to form the salt. X-ray crystallographic results have previously confirmed that organic salts rather than physical mixtures are formed when basic L-amino acids are reacted with alpha-keto analogs. U.S. Pat. No. 4,228,099.

The mixed salts employed in the mixtures of the present invention are formed by the reaction of the respective basic amino acid, such as L-histidine, L-ornithine, and L-lysine, with the desired alpha-keto analog of a branched-chain essential amino acids. These mixed salts may be represented by the following empirical formula:

AK·x H$_2$O wherein A is selected from the group consisting of L-ornithine, L-lysine, and L-histidine, and K is an alpha-keto analog of a branched-chain essential amino acid, selected from alpha-ketoisovalerate, alpha-ketoisocaproate, and alpha-keto-betamethylvalerate, and wherein x varies from 0 to about 1. In the case of the ornithine salt, there is no water of hydration and hence, x equals 0. The preparation of L-ornithine alpha-ketoisocaproate is described in U.S. Pat. No. 4,228,099 (column 3, line 59—column 4, line 42).

Effective daily dosages of the mixtures of the present invention will vary according to the weight of the patient, the severity of the condition, and other factors. Average daily doses, which are believed to be effective in the treatment of chronic renal failure, are given for the constituents of each of the six mixtures as follows:

Mixture A: 7 millimoles of L-ornithine alpha-ketoisocaproate, 14 millimoles of L-ornithine alpha-ketoisovalerate, 7 millimoles of L-lysine alpha-ketoisocaproate, 14 millimoles of L-lysine alpha-keto-beta-methylvalerate, and 4 millimoles of L-histidine alpha-ketoisocaproate.

Mixture B: 7 millimoles of L-ornithine alpha-keto isocaproate, 14 millimoles of L-ornithine alpha-keto-beta-methylvalerate, 7 millimoles of L-lysine alpha-ketoisocaproate, 14 millimoles of L-lysine alpha-ketoisovalerate, and 4 millimoles of L-histidine alpha-ketoisocaproate.

Mixture C: 7 millimoles of L-ornithine alpha-ketoisovalerate, 14 millimoles of L-ornithine alpha-keto-betamethylvalerate, 7 millimoles of L-lysine alpha-ketoisovalerate, 14 millimoles of L-lysine alpha-ketoisocaproate, and 4 millimoles of L-histidine alpha-keto-isocaproate.

Mixture D: 14 millimoles L-ornithine alpha-ketoisovalerate, 7 millimoles of L-ornithine alpha-keto-beta-methylvalerate, 14 millimoles of L-lysine alpha-ketoisocaproate, 7 millimoles of L-lysine alpha-keto-beta-methylvalerate, and 4 millimoles of L-histidine alpha-ketoisocaproate.

Mixture E: 14 millimoles of L-ornithine alpha-ketoisocaproate, 7 millimoles of L-ornithine alpha-ketoisovalerate, 7 millimoles of L-lysine alpha-ketoisovalerate, 14 millimoles of L-lysine alpha-keto-beta-methylvalerate, and 4 millimoles of L-histidine alpha-ketoisocaproate.

Mixture F: 14 millimoles of L-ornithine alpha-keto isocaproate, 7 millimoles of L-ornithine alpha-keto-beta-methylvalerate, 14 millimoles of L-lysine-alpha-ketoisovalerate, 7 millimoles of L-lysine alpha-keto-beta-methylvalerate and 4 millimoles of L-histidine alpha-ketoisocaproate.

The mixtures B, C and F are more palatable than other salt mixtures containing like proportions of basic amino acids and keto acids. Although the "EE" mixed salt supplement is significantly less unpalatable than supplements based on calcium salts of alpha-keto acids, the taste of the mixture is not a pleasant one. For patients receiving the supplement on a long term basis, the taste of the supplement is important. Consequently, mixtures B, C and F are preferred.

Mixtures B and C above omit the mixed salt constituent L-lysine alpha-keto-beta-methylvalerate which has been found to be difficult to crystallize and to be relatively unstable in comparison with other mixed salts. Consequently, dietary supplements formulated using these mixtures have relatively greater shelf life than other mixtures which supply the basic amino acids and alpha-keto analogs of branched-chain essential amino acids supplied by dietary supplement "EE." Thus, mixtures B and C are especially preferred.

While the mixtures of the present invention may be administered either orally or parenterally, they are especially adapted for oral administration. The mixtures are preferably administered by first dissolving or suspending them in a fruit juice, such as orange juice or grapefruit juice, or in another fluid such as water, which the patient subsequently consumes. It is especially preferred that the mixtures be dissolved or suspended in an acidic aqueous medium, such as grapefruit juice. The mixtures of the present invention may also be administered orally in a dry form, such as tablets or powder.

Although the mixed salts are believed to dissociate to some extent when initially mixed with the carrier, dissociation may not be complete, as different mixtures do not taste the same, as discussed below.

In addition to mixtures A through F specified above, compositions of the present invention may also contain other constituents of the "EE" dietary supplement, namely, L-tyrosine, L-threonine, and calcium D,L-alpha-hydroxy-gamma-methylthiobutyrate. As in the case of the mixtures of mixed salts of the present invention, the effective daily dosages of these additional constituents will vary according to the weight of the patient, the severity of the condition, and other factors. However, the average daily dosages of each of these additional constituents which have previously been found to be effective are as follows: L-tyrosine, 20 millimoles; L-threonine, 15 millimoles; calcium D,L-alpha-hydroxy-gamma-methylthiobutyrate, 2 millimoles.

In addition to these constituents of dietary supplement "EE," the mixtures of the present invention may be supplemented with vitamins and minerals, such as ascorbic acid (vitamin C), vitamin B complex, and calcium as, for example, calcium carbonate, or as "Neo-Calglucon," trademark of Sandoz Chemical for calcium gluconate. Further, the mixtures of the present invention are preferably administered in conjunction with a 20–30 gram per day protein diet.

Preferably, an "unselected" or "mixed" quality protein diet is used, because such diets permit considerable variety in the choice of foods, and consequently are relatively well accepted by patients, in comparison with "high" quality protein diets which require such foods as eggs and cottage cheese to provide "high" quality protein. Protein "quality" here refers to the proportion of essential amino acids provided by the protein in comparison with the non-essential amino acids provided. "Unselected" protein diets must usually be supplemented with a mixture of essential amino acids and/or their keto acid analogs.

The therapeutic efficacy for treatment of humans with chronic renal failure with mixed salts of basic amino acids and alpha-keto analogs of branched-chain essential amino acids has previously been documented, as discussed above. Because the mixed salt mixtures provide the same amino acids and keto acids as does supplement "EE," the therapeutic efficacy of dietary supplements containing the mixed salt mixtures of the present invention is expected to be the same as that previously established for dietary supplement "EE." Each of the mixed salt mixtures of the present invention and the mixed salt mixture of dietary supplement "EE" give identical quantities of L-ornithine, L-lysine, L-histidine, alpha-ketoisocaproate, alpha-ketoisovalerate, and alpha-keto-beta-methylvalerate.

The superior taste of mixed salt mixtures B, C and F of the present invention will now be described by the following specific example.

EXAMPLE 1

Six formulations of a dietary supplement providing like quantities of amino and keto acids identical to those of dietary supplement "EE" were prepared. As detailed in Table I above, each of the six formulations lacked two mixed salts. Each of the formulations was dissolved in grapefruit juice and the taste of each was ranked by 5 normal volunteers and by 10 patients with chronic renal failure (scale: 1=best, 6=worst). The results of the evaluation by normal volunteers are given in Table II below.

TABLE II

| Mixture | Sum of Rankings |
| --- | --- |
| A | 27 |
| B | 11 |
| C | 12 |
| D | 23 |
| E | 21 |
| F | 11 |

Friedman Statistic=14, degrees of freedom=5, $p \leq$ to 0.02. These results indicate that normal volunteers preferred the taste of mixtures B, C and F.

However, patients with chronic renal failure did not consistently discriminate among any of the mixtures. On the other hand, given the expected ability of dietary supplements having the amino acid and alpha-keto analog composition of dietary supplement "EE" to arrest the rate of progression of chronic renal failure, it is anticipated that mixtures of the present invention will be useful in treating patients having less severe renal failure than those participating in the above study. It is believed that the taste of such less severely afflicted patients is more accurately predicted by the results obtained with normal subjects than those obtained with patients suffering from severe chronic renal failure.

Taste tests conducted using the salt mixtures of the present invention both as dry powders and mixed with water and administered to normal subJects revealed no statistically significant taste preferences. Thus, the taste test results obtained using the grapefruit juice carrier are particularly surprising and unexpected.

The present invention may be embodied in other specific forms without departing from the spirit or essential attributes thereof and, accordingly, reference should be made to the appended claims, rather than to the foregoing specification, as indicating the scope of the invention.

We claim:

1. A method for the nutritional treatment of chronic renal failure comprising oral or parenteral administration of an effective dosage to subjects suffering from this condition of a composition comprising a mixture of salts which are the reaction product of a basic L-amino acid selected from the group consisting of L-ornithine, L-lysine, and L-histidine and a branched-chain essential amino acid alpha-keto acid analog selected from the group consisting of alpha-ketoisocaproate, alpha-ketoisovalerate, and alpha-keto-beta-methylvalerate, said mixture consisting essentially of no more than five of said salts including L-histidine alpha-keto-isocaproate as the source of L-histidine, said salts providing an average daily dosage of about 14 millimoles each of alpha-keto-beta-methylvalerate and alpha-ketoisovalerate and about 18 millimoles of alpha-ketoisocaproate.

2. A method according to claim 1 wherein said mixture excludes at least one of the salts L-ornithine alpha-ketoisovalerate and L-lysine alpha-keto-beta-methylvalerate.

3. A method according to claim 1 wherein said salts provide an average daily dosage of about 21 millimoles each of L-ornithine and L-lysine and about 4 millimoles of L-histidine.

4. A method according to claim 1 wherein said treatment additionally comprises the daily administration to subjects suffering from chronic renal failure of from about 20 g to 30 g of protein.

5. A method according to claim 4 wherein said protein is mixed-quality protein.

6. A method according to claim 1 wherein said treatment additionally comrpises the daily administration to subjects suffering from chronic renal failure of supplemental vitamins and minerals.

7. A method according to claim 6 wherein said supplemental vitamins and minerals comprise B complex vitamins, ascorbic acid, and calcium.

8. A composition for the nutritional treatment of chronic renal failure comprising a mixture of salts which are the reaction product of a basic L-amino acid selected from the group consisting of L-ornithine, L-lysine, and L-histidine and a branched-chain essential amino acid alpha-keto acid analog selected from the group consisting of alpha-ketoisocaproate, alpha-ketoisovalerate, and alpha-keto-beta-methylvalerate, said mixture consisting essentially of no more than five of said salts including L-histidine alpha-ketoisocaproate as the source of L-histidine, said salts providing the six amino acid constituents wherein the alpha-keto acid analogs are provided in proportions of about 14 millimoles each of alpha-keto-beta-methylvalerate and alpha-ketoisovalerate to about 18 millimoles of alpha-ketoisocaproate.

9. A composition according to claim 8 wherein said composition is adapted for daily administration to subjects with chronic renal failure, wherein said mixture consists essentially of about:

7 millimoles of L-ornithine alpha-ketoisovalerate,
14 millimoles of L-ornithine alpha-keto-beta-methylvalerate,
7 millimoles of L-lysine alpha-ketoisovalerate,
14 millimoles of L-lysine alpha-ketoisocaproate, and
4 millimoles of L-histidine alpha-ketoisocaproate.

10. A composition according to claim 8 wherein said composition is adapted to daily administration to subjects with chronic renal failure, wherein said mixture consists essentially of about:

7 millimoles of L-ornithine alpha-ketoisocaproate,
14 millimoles of L-ornithine alpha-keto-beta-methylvalerate,
7 millimoles of L-lysine alpha-ketoisocaproate,
14 millimoles of L-lysine alpha-ketoisovalerate, and
4 millimoles of L-histidine alpha-ketoisocaproate.

11. A composition according to claim 8 wherein said composition is adapted to daily administration to subjects with chronic renal failure, wherein said mixture consists essentially of about:

14 millimoles of L-ornithine alpha-keto-isocaproate,
7 millimoles of L-ornthine alpha-keto-beta-methylvalerate,
14 millimoles of L-lysine alpha-ketoisovalerate,
7 millimoles of L-lysine alpha-keto-beta-methylvalerate, and
4 millimoles of L-histidine alpha-ketoisocaproate.

12. A composition according to claim 8 wherein said composition is adapted to daily administration to subjects with chronic renal failure, wherein said mixture consists essentially of about:

7 millimoles of L-ornithine alpha-ketoisocaproate,
14 millimoles of L-ornithine alpha-ketoisovalerate,
7 millimoles of L-lysine alpha-ketoisocaproate,
14 millimoles of L-lysine alpha-keto-beta-methylvalerate, and
4 millimoles of L-histidine alpha-ketoisocaproate.

13. A composition according to claim 8 wherein said composition is adapted to daily administration to subjects with chronic renal failure, wherein said mixture consists essentially of about:

14 millimoles of L-ornithine alpha-ketoisovalerate,
7 millimoles of L-ornithine alpha-keto-beta-methylvalerate,
14 millimoles of L-lysine alpha-ketoisocaproate,
7 millimoles of L-lysine alpha-keto-beta-methylvalerate, and
4 millimoles of L-histidine alpha-ketoisocaproate.

14. A composition according to claim 8 wherein said composition is adapted to daily administration to subjects with chronic renal failure, wherein said mixture consists essentially of about:

14 millimoles of L-ornithine alpha-ketoisocaproate,
7 millimoles of L-ornithine alpha-ketoisovalerate,
7 millimoles of L-lysine alpha-ketoisovalerate, 14 millimoles of L-lysine alpha-keto-beta-methylvalerate, and
4 millimoles of L-histidine alpha-ketoisocaproate.

15. A composition according to claim 9 additionally comprising about:
20 millimoles of L-tyrosine,
15 millimoles of L-threonine, and
2 millimoles of calcium D,L-alpha hydroxy-gamma-methylthiobutyrate.

16. A composition according to claim 10 additionally comprising about:
20 millimoles of L-tyrosine,
15 millimoles of L-threonine and
2 millimoles of calcium D,L-alpha-hydroxy-gamma-methylthiobutyrate.

17. A composition according to claim 11 additionally comprising about:
20 millimoles of L-tyrosine,
15 millimoles of L-threonine and
2 millimoles of calcium D,L-alpha-hydroxy-gamma-methylthiobutyrate.

18. A composition according to claim 12 additionally comprising about:
20 millimoles of L-tyrosine,
15 millimoles of L-threonine, and
2 millimoles of calcium D,L-alpha hydroxy-gamma-methylthiobutyrate.

19. A composition according to claim 13 additionally comprising about:
20 millimoles of L-tyrosine,
15 millimoles of L-threonine, and
2 millimoles of calcium D,L-alpha-hydroxy-gamma-methylthiobutyrate.

20. A composition according to claim 14 additionally comprising about:
20 millimoles of L-tyrosine,
15 millimoles of L-threonine, and
2 millimoles of calcium D,L-alpha-hydroxy-gamma-methylthiobutyrate.

21. A composition according to claim 8 additionally comprising a carrier fluid.

22. A composition according to claim 21 wherein said carrier fluid is selected from water and fruit juices.

23. A composition according to claim 8 wherein said mixture excludes at least one of the salts L-ornithine alpha-ketoisovalerate and L-lysine alpha-keto-beta-methylvalerate.

24. A composition according to claim 8 additionally comprising amino acid constituents in proportions of about 20 millimoles L-tyrosine, about 15 millimoles L-threonine, and about 2 millimoles calcium D,L-alpha-hydroxy-gamma-methylthiobutyrate.

25. A composition according to claim 8 wherein the L-amino acid constituents are provided in the proportions of about 21 millimoles each of L-ornithine and L-lysine to about 4 millimoles of L-histidine, said proportions being relative to the proportions of alpha-keto acid analog constituents in claim 8.

* * * * *